United States Patent
Kruecker et al.

(10) Patent No.: US 11,583,697 B2
(45) Date of Patent: Feb. 21, 2023

(54) INTERVENTIONAL GUIDANCE SYSTEM WITH INTEGRATED TRACKING SETUP

(71) Applicant: KONINKLIJKE PHILIPS N.V., Eindhoven (NL)

(72) Inventors: Jochen Kruecker, Washington, DC (US); Shyam Bharat, Cortlandt Manor, NY (US); Cynthia Ming-Fu Kung, New York, NY (US); Christopher Stephen Hall, Kirkland, WA (US); Falk Uhlemann, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1817 days.

(21) Appl. No.: 14/424,282

(22) PCT Filed: Aug. 15, 2013

(86) PCT No.: PCT/IB2013/056656
§ 371 (c)(1),
(2) Date: Feb. 26, 2015

(87) PCT Pub. No.: WO2014/033583
PCT Pub. Date: Mar. 6, 2014

(65) Prior Publication Data
US 2015/0216619 A1    Aug. 6, 2015

Related U.S. Application Data

(60) Provisional application No. 61/693,824, filed on Aug. 28, 2012.

(51) Int. Cl.
*A61B 8/00* (2006.01)
*A61N 5/10* (2006.01)
(Continued)

(52) U.S. Cl.
CPC ........ *A61N 5/1001* (2013.01); *A61B 17/3403* (2013.01); *A61B 34/20* (2016.02);
(Continued)

(58) Field of Classification Search
CPC ................ A61B 2034/2051; A61B 2034/2072
See application file for complete search history.

(56) References Cited

U.S. PATENT DOCUMENTS 5,729,129 A    3/1998  Acker
5,787,886 A *  8/1998  Kelly .................... A61B 34/20
                                                          600/407
(Continued)

FOREIGN PATENT DOCUMENTS

JP    H11506831 A    6/1999
JP    2004148127 A   5/2004
(Continued)

*Primary Examiner* — Rajeev P Siripurapu (57) ABSTRACT

A system with integrated tracking includes a procedure-specific hardware component (112 or 116) disposed at or near a region of interest. A field generator (114) is configured to generate a field with a field of view covering the region of interest. A mounting device (115) is connected to the field generator and is coupled to the procedure-specific hardware. The field generator is fixedly positioned by the mounting device to permit workflow access to the region of interest without interfering with the field generator and to provide a known position of the field generator relative to the region of interest. A tracking device (110) is configured to be inserted in or near the region of interest to be tracked within the field of view of the field generator to generate tracking data.

7 Claims, 5 Drawing Sheets

(51) Int. Cl.
  *A61B 17/34* (2006.01)
  *A61B 34/20* (2016.01)
  *A61B 17/00* (2006.01)
(52) U.S. Cl.
  CPC ......... *A61N 5/1007* (2013.01); *A61N 5/1049* (2013.01); *A61B 2017/00274* (2013.01); *A61B 2017/3411* (2013.01); *A61B 2034/2051* (2016.02); *A61B 2034/2072* (2016.02); *A61N 2005/1012* (2013.01); *A61N 2005/1051* (2013.01); *A61N 2005/1058* (2013.01)

(56) References Cited

U.S. PATENT DOCUMENTS

| | | | |
|---|---|---|---|
| 8,145,290 | B2 | 3/2012 | Kindlein |
| 2003/0084909 | A1 | 5/2003 | Burdette et al. |
| 2003/0229282 | A1* | 12/2003 | Burdette .................. A61N 5/00 600/439 |
| 2004/0199072 | A1 | 10/2004 | Sprouse et al. |
| 2007/0238982 | A1 | 10/2007 | Caylor, III |
| 2008/0097195 | A1 | 4/2008 | Urquhart et al. |
| 2008/0216239 | A1 | 9/2008 | Luginbuhl et al. |
| 2009/0118724 | A1* | 5/2009 | Zvuloni .................. A61N 7/02 606/27 |
| 2009/0154293 | A1 | 6/2009 | Sengupta et al. |
| 2010/0016710 | A1 | 1/2010 | Kumar et al. |
| 2010/0057157 | A1 | 3/2010 | Govari et al. |
| 2011/0071389 | A1 | 3/2011 | Simon et al. |
| 2011/0224537 | A1 | 9/2011 | Brimmer |
| 2012/0165595 | A1 | 6/2012 | Kindlein |
| 2013/0096422 | A1* | 4/2013 | Boctor ................. A61B 5/0095 600/424 |

FOREIGN PATENT DOCUMENTS

| | | | | |
|---|---|---|---|---|
| JP | 2005118553 | A | 5/2005 | |
| JP | 4634859 | A | 11/2006 | |
| JP | 2007021216 | A | 2/2007 | |
| JP | 2010063880 | A | 3/2010 | |
| WO | 2011100753 | A2 | 8/2011 | |
| WO | WO-2011100753 | A2 * | 8/2011 | .......... A61B 5/0095 |
| WO | 2011158113 | A1 | 12/2011 | |

* cited by examiner

INTERVENTIONAL GUIDANCE SYSTEM WITH INTEGRATED TRACKING SETUP

This application is a national stage application under 35 U.S.C. § 371 of International Application No. PCT/IB2013/056656 filed on Aug. 15, 2013 and published in the English language on Mar. 6, 2014 as International Publication No. WO 2014/033583 A1, which claims priority to U.S. Application No. 61/693,824 filed on Aug. 28, 2012, the entire disclosures of which are incorporated herein by reference.

This disclosure relates to tracking instruments and more particularly to systems and methods for navigation-assisted therapy with integrated tracking devices.

Brachytherapy (including low-dose rate (LDR) and high-dose rate (HDR) brachytherapy) is one of the most common treatment modalities for prostate cancer. In LDR brachytherapy, radioactive seeds are permanently implanted into the prostate using trans-perineal needle access to the prostate through a grid template with the aid of transrectal ultrasound (TRUS) image guidance. In HDR brachytherapy, catheters are temporarily implanted into the prostate trans-perineally with TRUS guidance, followed by computer-controlled temporary insertion of a high-dose rate radioactive source into the catheters.

For both methods (LDR and HDR), the grid and TRUS probe are mounted on a stepper which helps to stabilize the setup. Both methods (LDR and HDR) have proven very effective in curing prostate cancer, but both suffer from variable and potentially severe side effects, variable clinical outcomes depending on the experience of the operator, and cumbersome clinical workflows.

In accordance with the present principles, a system with integrated tracking includes a procedure-specific hardware component disposed at or near a region of interest. A field generator is configured to generate a field with a field of view covering the region of interest. A mounting device is connected to the field generator and is coupled to the procedure-specific hardware. The field generator is fixedly positioned by the mounting device to permit workflow access to the region of interest without interfering with the field generator and to provide a known position of the field generator relative to the region of interest. A tracking device is configured to be inserted in or near the region of interest to be tracked within the field of view of the field generator to generate tracking data.

A brachytherapy system with integrated tracking includes a grid employed in a brachytherapy procedure for guiding treatment devices into or near a region of interest. An electromagnetic (EM) field generator is configured to generate an EM field with a field of view covering the region of interest. A mounting device is connected to the field generator, the field generator being fixedly positioned by the mounting device to permit workflow access to the region of interest without interfering with the field generator and to provide a known position of the field generator relative to the region of interest. A tracking device includes an EM sensor configured to be inserted in or near the region of interest to be tracked within the field of view of the field generator to generate tracking data. An actuating device is configured to move an imaging probe and being coupled to the mounting device to concurrently hold the field generator fixed.

A method for integrated tracking includes providing a field generator configured to generate a field with a field of view covering a region of interest; mounting the field generator to a procedure-specific hardware component disposed at or near the region of interest, the field generator being fixedly positioned by the mounting device to permit access to the region of interest without interfering with the field generator; and tracking a tracking device inserted in or near the region of interest within the field of view of the field generator to generate tracking data for a position of the tracking device.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, systems and methods are disclosed having small, lightweight and customized tracking devices. The tracking devices may include EM tracking devices including a field generator (FG). The FG can be directly connected to interventional procedure hardware or integrated into the hardware to harness benefits of tracking-assisted interventions without additional and cumbersome setups and calibration procedures and without obstructing access to conventionally used equipment.

Electromagnetic (EM) tracking permits more accurate deposition of low-dose rate (LDR) seeds and high-dose rate (HDR) catheters, mapping and monitoring of LDR seeds and HDR catheters and an adaptive workflow in which plan creation, execution and iterative plan updating are tightly integrated to ensure optimal delivery of the therapeutic dose. EM tracking involves setting up a field generator (FG) close to the patient, positioned such that the field-of-view of the generator covers an access path and a region of interest for the intervention (e.g., a prostate and surrounding tissue).

Conventional FGs have considerable weight and size. Vendors of FGs therefore offer mounting arms that are sturdy enough to support the weight of the FG, keep it in a fixed position, and connect to, e.g., a surgical table or patient bed. When the FG is used to guide a clinical procedure, the manual and separate mounting and positioning of the conventional FG is afflicted with several problems. These problems may include the following. Set up and positioning the FG is an additional step that costs time and lengthens the duration of the procedure. Repetitive motion injury is a risk for a person tightening/releasing a locking mechanism of the arm. If the arm fails or the locking mechanism is insufficiently tightened, possible injury to the patient may occur if the FG falls onto the patient. The accuracy of the tracking in regions of interest depends on appropriate positioning of the FG. With manual and separate mounting of the FG, the position of the FG relative to the regions of interest is variable as is the accuracy of the tracking information. This has significant negative impact on the efficacy of EM tracking in clinical procedures. The FG and mounting arm take up space and may obstruct the conventional workflow (e.g., blocking access to other equipment, reading of displays, etc.).

In particularly useful embodiments, a small and lightweight field generator is part of an electromagnetic (EM) tracking system and can be attached to a transrectal ultrasound (TRUS) stepper or other equipment, such that a field of view of the generator covers a region of interest (e.g., the prostate) of a patient and can be used to guide and monitor procedures (e.g., brachytherapy procedures). The lightweight FG(s) is designed and constructed to be flexible in application, with a field of view large enough to address a variety of possible clinical or non-clinical applications, and to be mounted with a separate mounting arm on or with other clinical hardware near a region of interest. EM tracking is an example of one navigational approach, although other navigational approaches are contemplated.

The present principles find application in any clinical navigation-assisted therapy. In particular, a brachytherapy solution (e.g., LDR and HDR) for prostate or other target organs will be described as examples. Other navigation solutions, using EM or other tracking technologies are also contemplated.

It should be understood that the present invention will be described in terms of medical instruments; however, the teachings of the present invention are much broader and are applicable to other instruments where navigation is needed for precise location or placement. In some embodiments, the present principles are employed in tracking or analyzing complex biological or mechanical systems. In particular, the present principles are applicable to internal tracking procedures of biological systems, radiation sources, medications, etc. and can be related to procedures in all areas of the body such as the lungs, gastro-intestinal tract, prostate, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software, in association with the appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk read/write (CD-RW), Blu-Ray™ and DVD.

Figure 1:
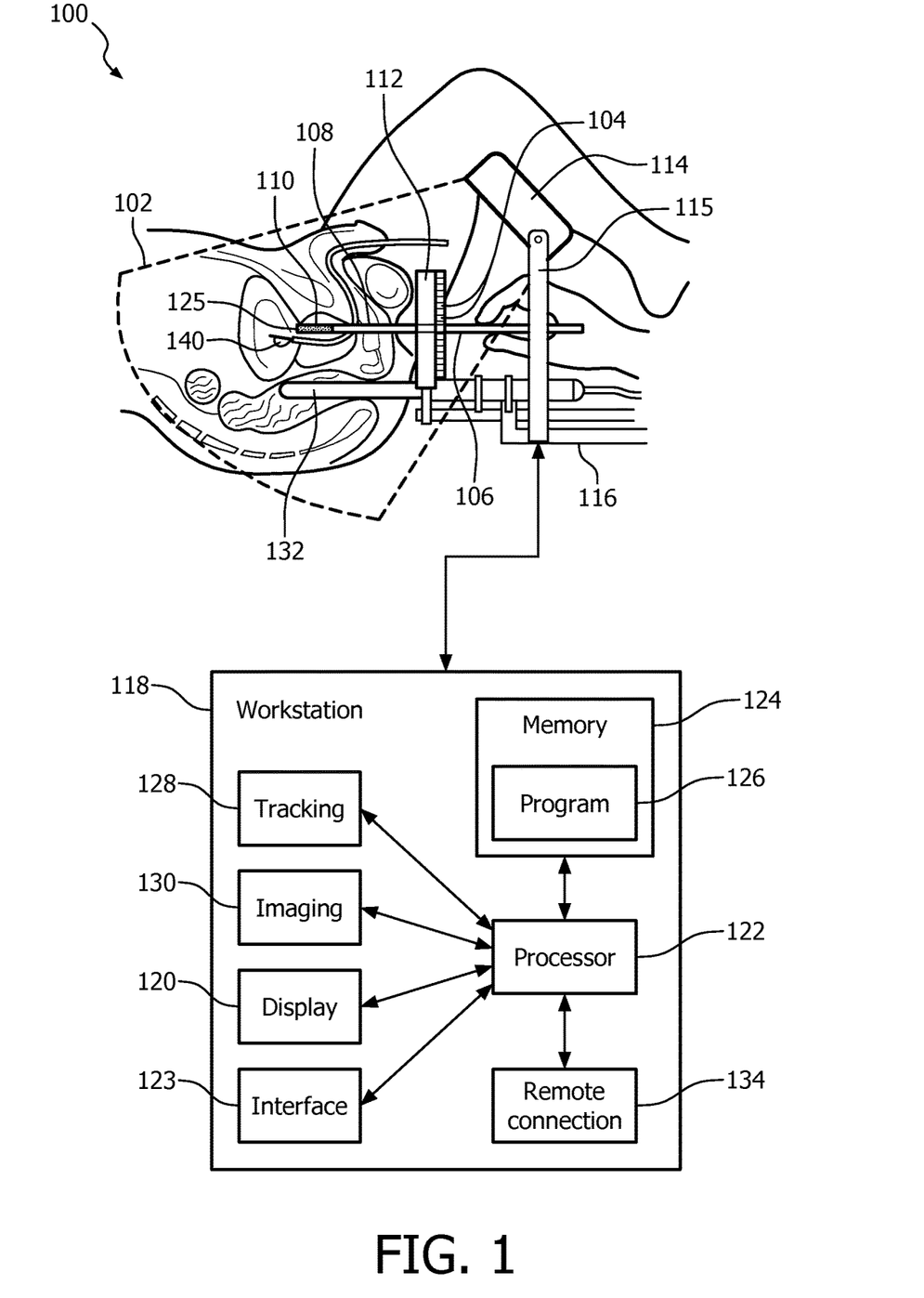
FIG. 1 is a block/flow diagram showing an illustrative guidance system with an integrated tracking system for a medical procedure (e.g., brachytherapy) in accordance with the present principles.

Referring now to the drawings in which like numerals represent the same or similar elements and initially to FIG. 1, an illustrative system 100 is depicted which employs tracking with a brachytherapy setup in accordance the present principles. System 100 illustratively depicts and employs an EM tracking navigation system 128 for tracking the placement of radioactive seeds or catheters in brachytherapy using EM tracking EM tracking or other navigation approaches need to have at least their positional accuracy checked to ensure the proper placement of seeds during a procedure. The system 100 employs a tracking sensor or sensors 110 attached to one or more devices (needles 108, catheters 106, etc.) to measure a position of the sensor 110 relative to a field generator (FG) 114. Other tracking technologies that may be employed include, e.g., optical, fiber-optical, acoustical or mechanical tracking technologies, which may be employed in addition to or instead of EM tracking. In addition, the present principles may be applicable and/or customized for procedures other than prostate brachytherapy, e.g., brachytherapy of the liver, breast, etc., non-brachytherapy prostate applications such as prostate biopsy, prostate ablations, or other therapy procedures for the prostate or other organs.

Therapy devices 108 (such as e.g., brachytherapy needles) include the tracking sensor 110 mounted thereon or therein. The sensor 110 may include an EM sensor although other sensors may be employed. A brachytherapy grid or template 112 is employed to locate a position as a starting point for introducing needles or other objects into a patient, and this permits guidance when forcing the needle 108 through one or a plurality of holes 104 inside the grid 112. The grid 112 includes a plurality of holes 104 to act as guides for placement of needles or other therapy devices 108 into the patient. The tracking sensors 110 are responsive to a magnetic field generator 114. For purposes of this disclosure, grid and template will be used interchangeably. The use of either grid or template alone includes the other.

A mounting device or holder 115 is configured to receive the field generator (FG) 114 immediately behind or coupled with the grid or template 112. In one embodiment, the FG 114 is coupled to a stationary position on an actuating device, such as, a stepper 116. The stepper 116 provides controlled motion for advancing and retracting a probe 132, such as an ultrasonic probe. In some embodiments, the grid 112 and/or the FG 114 may be actuated by the stepper 116 or may be coupled to a stationary or fixed portion of the stepper 116 (to include a fixed position during a procedure). A field of view 102 of the FG 114 includes an area or region of interest 140 (e.g., the prostate and surrounding tissue). Tracking information from the sensor 110 inside the needle 108 (e.g., inside the needle tip) is acquired by the tracking system 128 and then may be further processed on a processing workstation 118 and rendered on a display unit 120.

The tracking system 128 may include, e.g., the Aurora™ system (by Northern Digital Inc., Waterloo, ON, Canada). The field generator 114 and the tracking system 128 (control unit), are positioned such that a tracked needle tip 125 is in the field of view 102 of the field generator 114 for all positions inside the area of interest 140 and at the surface of the grid or template 112. Tracking data is transferred from the tracking system 128 to the workstation 118 in real-time. On the workstation 118, tracking data is stored, processed and visualized. The workstation 118 runs software programs (e.g., program module 126) to track devices such as a catheter 106 and/or a needle 108 and for planning a procedure.

The workstation 118 may include a console from which a procedure is supervised and/or managed. Workstation 118 preferably includes one or more processors 122 and memory 124 for storing programs and applications. An imaging system 130 may be provided and employed during a procedure. Imaging system 130 collects imaging data using, e.g., the probe 132 and renders the data on display 120. In one embodiment, the imaging system 130 may be employed to generate data on a position of the needle 108 (or catheter 106). In one embodiment, the imaging system 130 includes an ultrasonic imaging system. The ultrasonic probe 132 may be connected to the stepper 116 for use during a procedure.

Memory 124 may store programs for controlling the stepper 116 to move a position of the probe 132. The memory 124 may include a program module 126 that registers tracking data with image data to provide a physician with information about the placement of medication or treatment materials and the effectiveness of treatment. Module 126 may permit initialization of the grid 112, stepper 116, navigation and ultrasound equipment (imaging system 130) with the tracked needle(s) 108. To check the accuracy of needle placement, the tracked needle(s) 108 are inserted into one or more grid holes 104. This includes inserting one or several spatially tracked needles 108 into one or several holes 104 and advancing the needles 108 into the area of interest 140. The module 126 records position tracking data from the tracking system 128, which is gathered from the inserted needles 108 (and/or catheter 106) with the sensor(s) 110. The module 126 registers the recorded data with images collected from the imaging system 130.

Module 126 may be configured to provide workflow instructions for a user through use of an interface 123 and/or display 120 for reviewing process steps, tracking data and archiving data. The module 126 may perform the following tasks and features. The module 126, using the display 120 and the user interface 123, prompts and guides the user to follow a specific workflow or may be employed for generating a plan before a procedure is performed. The interface 123 may include a keyboard, mouse, a joystick, a haptic device, or any other peripheral or control to permit user feedback from and interaction with the workstation 118. The module 126 acquires and stores needle tracking data from each insertion of the tracked needles 108 into the grid holes 104. Each data set may be referred to as a "needle track".

The system 100 may include a remote connection 134 for remote data transfer to an agent outside the setting where the system 100 is being employed (e.g., the vendor or service contractor of the system 100) or for other uses.

In particularly useful embodiments, the FG 114 is sufficiently small and lightweight to be mounted directly on a part of conventionally used interventional hardware. The size of the FG 114 is preferably sufficient to permit full access during the workflow of a procedure and may have a plurality of sizes and shapes. The weight of the FG 114 is preferably less than 5 pounds and more preferably less than one pound, and in some instances may be a few ounces. The FG 114 is connected with the mounting device or holder 115, which may have adjustment capability. The mounting device 115 is preferably mounted in a fixed position relative to the region of interest 140 in the patient (e.g., on a stationary base of stepper 116 when employed for brachytherapy procedures). The FG 114 may be integrated into such devices as, e.g., the grid 112, be inserted into a patient bed or mattress, etc. The FG 114 is mounted such that it does not obstruct access to and/or use of the interventional hardware that it attaches to. The FG 114 can be mounted permanently or be repeatably positioned (in a same position after an interval of time) on the interventional hardware, or the FG 114 may be integrated with or in the hardware to provide an inherent fixed co-registration between the EM tracking and the ultrasonic or other imaging. This is particularly useful since it eliminates or reduces setup time, and eliminates variability in tracking accuracy. In other words, the FG 114 can be mounted to hardware that provides unobstructed access and reliable (repeatable) positioning of the FG 114. The position selected will provide accurate tracking without lost setup time or danger to the patient, personnel or equipment.

The FG 114 in accordance with the present principles has optimized tracking accuracy in a relatively small field of view (102) that is needed for a specific interventional procedure (e.g. covering the prostate, bladder, rectum, perineum, etc. for brachytherapy or other procedures). The FG 114 is configurable such that the field generation is adapted and/or shielded to provide robust operation in the presence of other hardware. In addition, the FG 114 may be placed in different positions, have different configurations and provide different functions as will be described herein.

Figure 2:
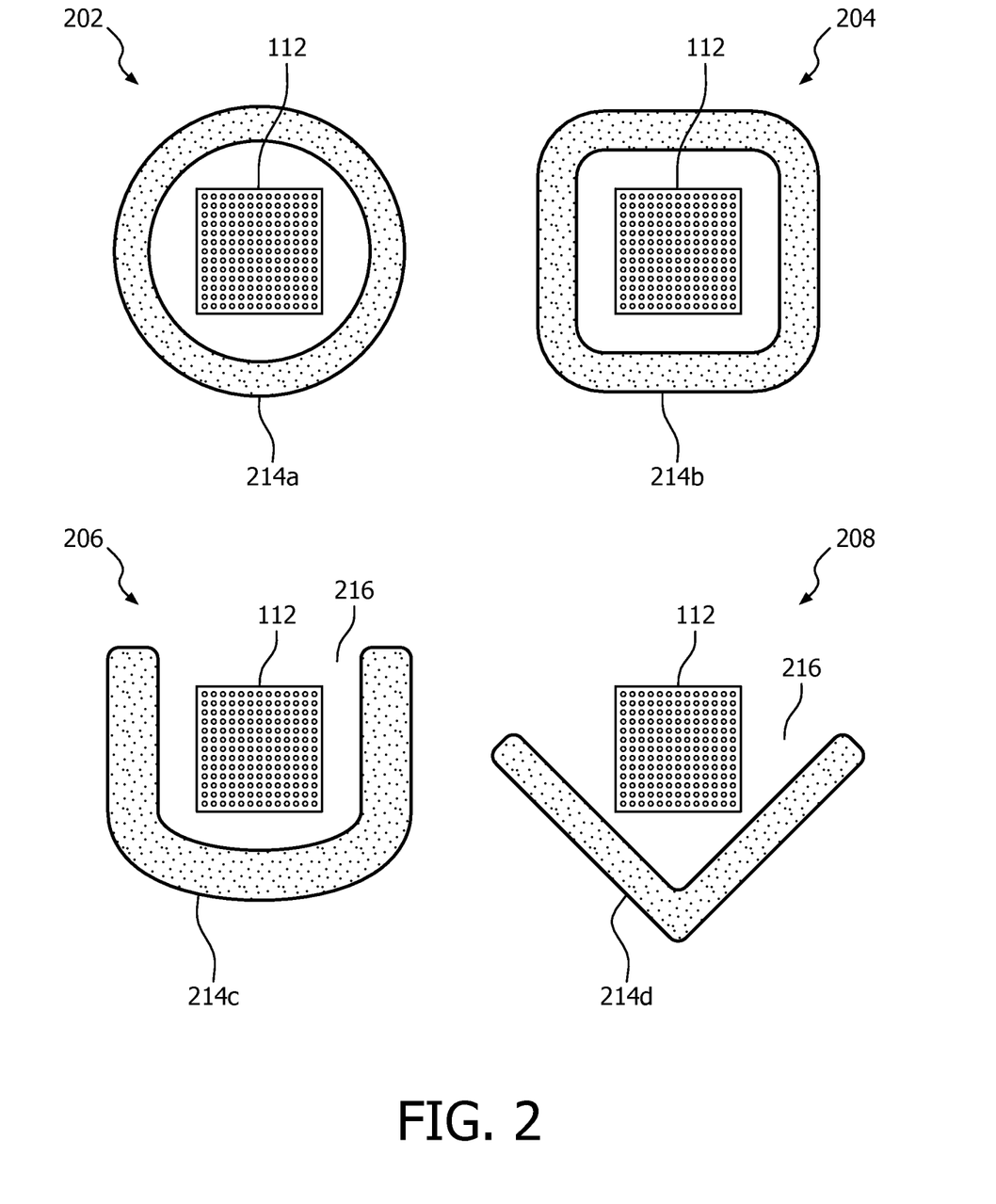
FIG. 2 shows four configurations of a field generator integrated with or positioned relative to a grid in accordance with illustrative embodiments.

Referring to FIG. 2, field generator configurations 202-208 are illustratively depicted. The FGs 214a-214d are preferably miniaturized in size and weight to permit placement at or near a region of interest. In addition, by reducing the size and weight, the FGs 214a-214d can be mounted, e.g., on a stepper, such as a trans-rectal ultrasound (TRUS) stepper, without exceeding the mechanical specifications of the stepper, or of a mounting arm holding the stepper. In some embodiments, the FGs 214a-214d (or 114) are rigidly attached to a fixed portion of the stepper (116), such as its base and positioned such that optimal tracking accuracy is obtained in a region encompassing a region of interest (e.g., prostate) and surrounding organs for a range of typical patient setups and patient anatomies.

Configurations 202, 204, 206 and 208 are examples of a shape of the FGs 214a-214d to accommodate a grid or template 112 and provide improved access to the grid 112. Configuration 202 includes an "O" shape that encircles outer edges of the grid 112. Configuration 204 includes a square or rectangular shape that follows or is proportional to the dimensions of the grid 112. Configurations 206 and 208 include a "U" shape and a "V" shape, respectively, that partially encircle outer edges of the grid 112. Configurations 206 and 208 of FGs 214c-214d provide an open internal "window" for better access to the grid 112 by providing at least one open side 216 about the grid 112. Other configurations of the FG 214 are also contemplated, e.g., ovals, straight or curved bars, etc.

The FG 214 may be integrated into interventional hardware devices, e.g., the template/grid 112 may be attached to or be a part of the FG 214. The FG 214 may be integrated or can be inserted into other hardware, such as a patient table or mattress (e.g., embedded in the table of mattress) and/or fixed at a known location (on the stepper, etc.).

Figure 3:
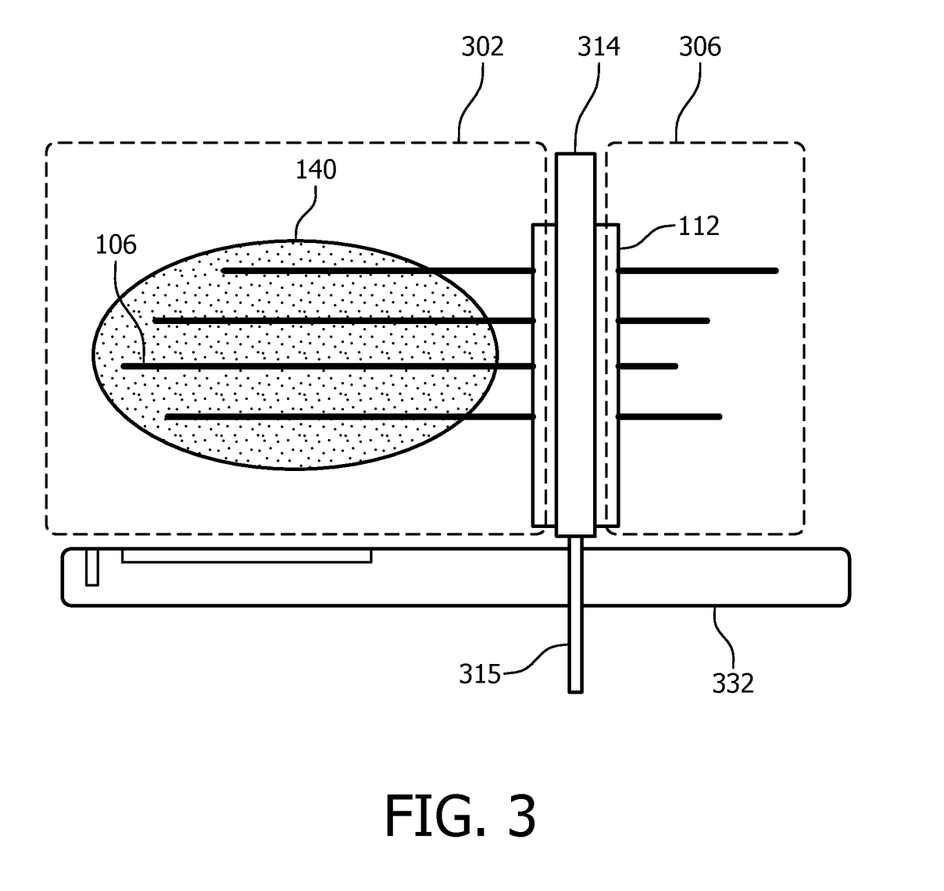
FIG. 3 is a side view showing a field generator configured to generate bi-directional tracking fields on two sides of the grid in accordance with one embodiment.

In addition to shape configurations and position configurations, the FG may include form factor configurations. Referring to FIG. 3, a field generator (FG) 314 is provided that surrounds the grid 112 and provides a first tracking field 302 in a direction of the region of interest 140, e.g., the prostate, and a second tracking field 306 in an opposite direction of the first tracking field 302 relative to FG 314. The directional fields may be provided using differently oriented coil windings in portions of the FG 314. The FG 314 may house a plurality or windings, magnets, etc. The FG 314 (or any other embodiment) can be fully integrated into the grid 112 to avoid mounting and calibration relative to the grid 112. (See e.g., FIG. 2).

By providing two tracking fields 302 and 306, devices such as catheters 106 (or needles 108), etc. can be tracked on both sides of the grid 112. Positions may be correlated as a check on registration between imaging and tracked devices. In addition, the grid 112 and the FG 314 may be connected by a same mounting member 315 to a stepper (116). A TRUS probe 332 may also be coupled to the stepper (116 on an actuated portion).

Figure 4:
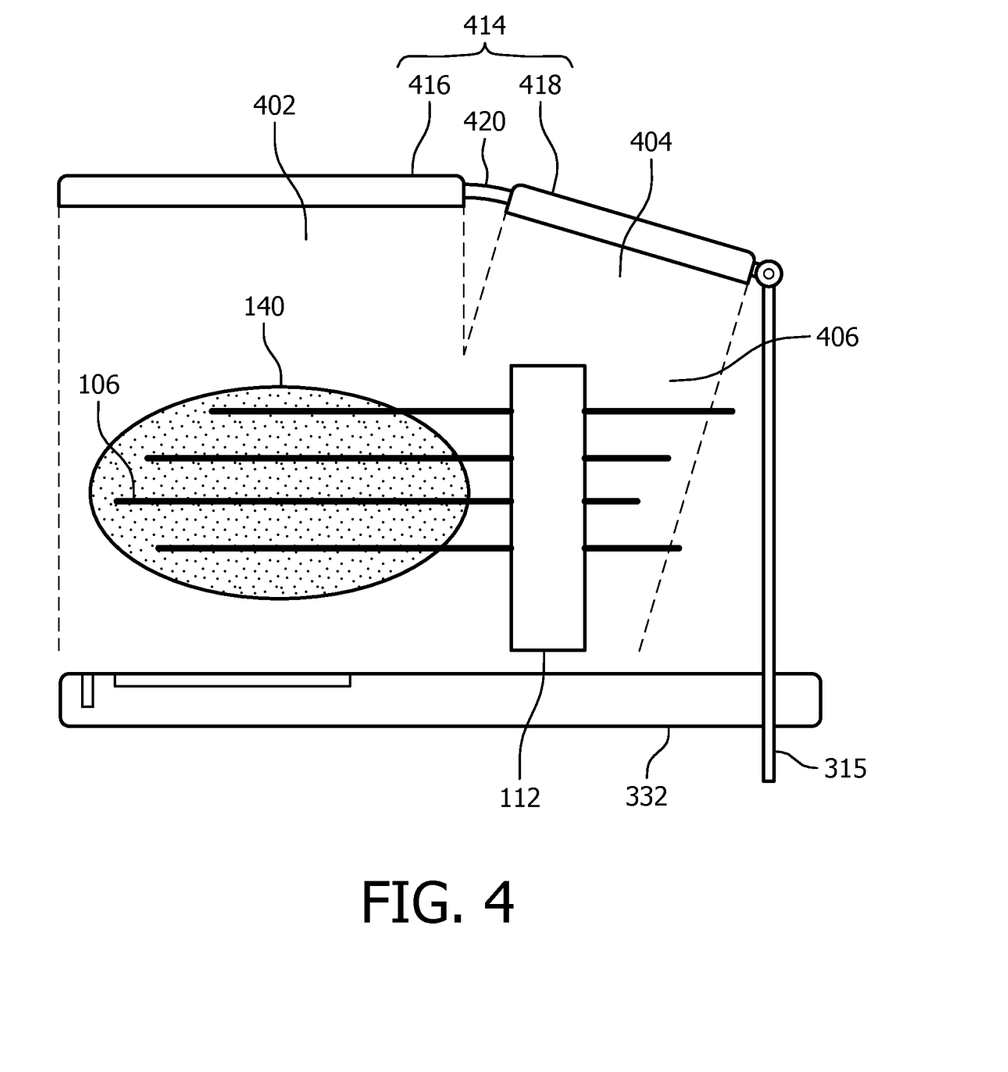
FIG. 4 is a side view showing a field generator configured to generate overlapping tracking fields in accordance with one embodiment.

Referring to FIG. 4, another field generator 414 is provided that covers two overlapping tracking fields of view. One field of view 402 includes the region of interest 140. Another field of view 404 includes a part of the region of interest 140 and a grid region 406. The unconventional form factor with multiple fields of view covers both the grid space and region of interest (e.g., prostatic) space to permit cross-reference data between the fields of view to assist in registration of different spaces and other benefits.

In the depicted embodiment, the FG 414 includes two field generating portions 416 and 418 corresponding with the two overlapping tracking fields of view 402 and 404, respectively. It should be understood that additional portions may be employed and that their configurations (e.g., shape, position and mounting) may be varied. For example, the FG 414 (or any other embodiment) may be mounted above the grid 112 so as not to obstruct access to the grid 112. The FG 414 (or any other embodiment) can also be mounted at the same level as the grid 112, provided it has an open internal "window" (or similar form factor) that enables easy access to the grid 112. The FG 414 (or any other embodiment) can also be mounted below the grid 112 and/or below the region of interest 140 (e.g., in a patient bed). For example, the FG 414 may be provided in a mattress or base of a patient bed and the patient may have the region of interest 140 positioned over the FG 414. This configuration may be employed with any of the embodiments described herein.

The FG 414 (or any other embodiment) may include a number of discrete mounting options or adjustments using the mounting member or device 315, such as a change of angle or distance from the grid 112, to optimize tracking accuracy for individual patients or permit the use or introduction of different hardware, instruments, etc. For FG 414, a connector 420 may be pivotally joined with or fixedly attached to the portions 406 and 408. An angular relationship between portions 416 and 418 may be achieved by making adjustments between the portions to accommodate a patient or a surgical/procedural scenario.

While the present principles are illustratively described in terms of exemplary embodiments, other embodiments are also contemplated. For example, instead of an EM FG, the customized tracking system component can be an optical source for optical tracking, an ultrasonic source for acoustic tracking, or any other component of a different tracking system technology. In addition, instead of mounting on a stepper, the customized tracking component can be mounted on other hardware that is employed for clinical procedures (such as head clamps, immobilization devices, etc.). The present principles can be applied in a variety of clinical settings, including diagnostic, therapeutic, surgical and interventional procedures. The procedures may include (but are not limited to) brachytherapy, ablation, trans-perineal biopsy, or surgical resection of the prostate or other organs. The present embodiments also find utility in any system that supports procedures with spatial tracking including tracking outside of the medical field.

Figure 5:
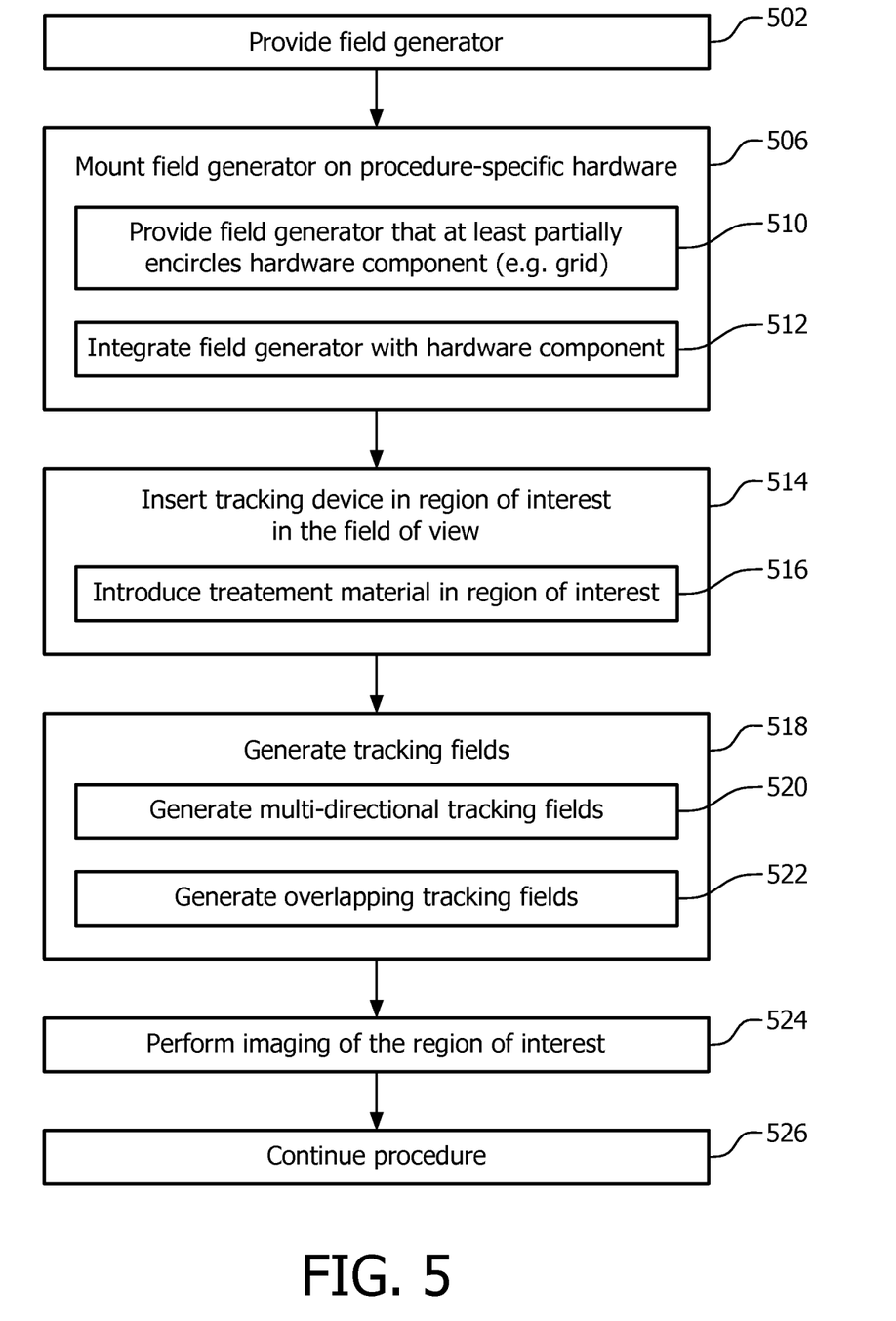
FIG. 5 is a block/flow diagram showing a method for tracking a treatment device in accordance with the present principles.

Referring to FIG. 5, a method for integrated tracking is illustratively described. In block 502, a field generator is provided that is configured to generate a field with a field of view covering a region of interest. The region of interest may include a prostate gland or other anatomical structure. In block 506, the field generator is preferably mounted to a procedure-specific hardware component disposed at or near the region of interest.

The field generator is positioned by a mounting device to permit access to the region of interest without interfering with the field generator during procedural workflow. The procedure-specific hardware may include a template or grid employed in a brachytherapy procedure or may include a stepper or actuation mechanism, and the stepper is employed for mounting the field generator.

In one embodiment, the procedure-specific hardware component may include a grid, and the field generator at least partially encircles the grid permitting access to the grid through the field generator in block 510. In block 512, the field generator is integrated with the procedure-specific hardware component. The field generator may be configured to include one of a closed shape or an open shape about a perimeter of the grid (e.g., a circle or square, U or V, etc.).

In block 514, a tracking device is inserted in or near the region of interest within the field of view of the field generator, is tracked and generates tracking data to indicate a position of the tracking device. The field generator may include an electromagnetic (EM) field generator, and the tracking device may include an EM sensor. Other field generating technologies may be employed. In one embodiment, treatment material is introduced with the tracked device to determine a position of the treatment material in the region of interest in block 516.

In block 518, tracking fields are generated to track the tracking devices in the region of interest. In block 520, tracking fields may be generated in at least two directions with the field generator to concurrently provide fields of view in a plurality of regions. The plurality of regions may include the region of interest and one other region. In block 522, tracking fields may be generated in at least two overlapping regions with the field generator, wherein the field generator includes a plurality of portions configured to generate the at least two overlapping regions. The at least two overlapping regions may provide redundant tracking data to locate the tracking device.

In block 524, concurrent imaging may be performed to provide tracking data or to better understand internal events.

The imaging may include ultrasonic imaging (e.g. TRUS) using a probe. In block 526, the procedure continues until planned goals are achieved.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for interventional guidance system with integrated tracking setup (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A brachytherapy system with integrated tracking, comprising:
a grid block employed in a brachytherapy procedure for guiding a treatment device into or near a region of interest interior to a patient;
an electromagnetic (EM) field generator configured to generate a magnetic field with a field of view covering the region of interest, wherein the electromagnetic (EM) field generator surrounds the grid block;
a mounting device mechanically connected with the electromagnetic (EM) field generator and the grid block, the electromagnetic (EM) field generator being fixedly positioned by the mounting device exterior to the patient to provide a mechanically fixed, known position of the electromagnetic (EM) field generator relative to the grid block and the region of interest;
a magnetic field sensor configured to (1) be mounted to a portion of the treatment device which is configured to pass through the grid block and (2) be inserted in or near the region of interest interior to the patient to be tracked within the field of view of the electromagnetic (EM) field generator to generate tracking data;
an ultrasonic imaging probe configured to be inserted into the patient to generate ultrasound images of the region of interest; and
an actuating device configured to move the ultrasonic imaging probe relative to the grid block and the region of interest and being separately coupled to the mounting device to hold the electromagnetic (EM) field generator fixed as the ultrasonic imaging probe is moved.

2. The system as recited in claim 1, wherein the treatment device includes one of a needle or a catheter.

3. The system as recited in claim 1, further including at least one of a rigid catheter or a rigid needle with an end portion configured to be inserted through the grid block into tissue in the region of interest to insert brachytherapy seeds, the magnetic field sensor being connected with the end portion of the at least one rigid catheter or rigid needle.

4. The system as recited in claim 1, further including:
an ultrasound imager;
a stepper, the grid block and the electromagnetic (EM) field generator being stationarily mounted to a base of the stepper, the stepper being configured to move the ultrasound imager relative to the grid block and the electromagnetic (EM) field generator.

5. The system as recited in claim 1, wherein the electromagnetic (EM) field generator is integrated with the grid block.

6. The system as recited in claim 1, wherein the actuating device includes a stepper configured to move the ultrasonic imaging probe relative to the grid block and a base fixedly mounted with the grid block, the mounting device being fixedly mounted to the base such that the stepper moves the ultrasonic imaging probe in a series of mechanically fixed positions relative to the electromagnetic (EM) field generator, the grid block, and the region of interest.

7. A system with integrated tracking, comprising:
a brachytherapy procedure-specific hardware disposed at or near a region of interest interior to a patient, wherein the brachytherapy procedure-specific hardware includes at least one both a grid and a stepper employed in the brachytherapy procedure, wherein the brachytherapy procedure-specific hardware is configured to be mounted in a fixed spatial relationship to the region of interest, wherein the grid is fixedly mounted to the stepper, and wherein the grid includes bores configured to guide brachytherapy seed carrying brachytherapy needles in or near the region of interest interior to the patient;
a field generator configured to generate a field with a field of view covering the region of interest, the field generator is an electromagnetic (EM) field generator;
a mounting bracket connected to the field generator and mechanically coupled to the brachytherapy procedure-specific hardware, wherein the mounting bracket is mechanically coupled to the at least one of the grid and the stepper, and wherein the field generator is fixedly positioned by the mounting bracket to permit workflow access to the region of interest without interfering with the field generator and to provide a known position of the field generator relative to the region of interest;
a field sensor configured to be inserted in or near the region of interest interior to the subject to be tracked within the field of view of the field generator to generate tracking data wherein the field sensor is an electromagnetic field sensor mounted adjacent a tip of one of the brachytherapy needles and the tracking data is indicative of a location of the tip of the brachytherapy needle relative to the region of interest interior to the patient; and
an ultrasound imaging probe mounted to the stepper, the stepper being configured to move the ultrasound imaging probe relative to the region of interest while the grid, the stepper, the mounting bracket, and field generator remain stationary relative to the region of interest.

\* \* \* \* \*